United States Patent
Doubler et al.

(10) Patent No.: US 6,887,242 B2
(45) Date of Patent: May 3, 2005

(54) SPLIT RING BONE SCREW FOR A SPINAL FIXATION SYSTEM

(75) Inventors: Robert L. Doubler, Ida, MI (US); John E. Hammill, Rossford, OH (US)

(73) Assignee: Ortho Innovations, LLC, Toledo, OH (US)

( * ) Notice: Subject to any disclaimer, the term of this patent is extended or adjusted under 35 U.S.C. 154(b) by 176 days.

(21) Appl. No.: 10/067,687

(22) Filed: Feb. 4, 2002

(65) Prior Publication Data

US 2003/0073997 A1 Apr. 17, 2003

Related U.S. Application Data

(63) Continuation-in-part of application No. 09/981,961, filed on Oct. 17, 2001, now Pat. No. 6,623,485.

(51) Int. Cl.⁷ ............................................... A61B 17/56
(52) U.S. Cl. .......................................... 606/61; 606/73
(58) Field of Search ............................ 606/61, 73, 60, 606/69, 70, 71, 72

(56) References Cited

U.S. PATENT DOCUMENTS

| | | | |
|---|---|---|---|
| 4,241,463 A | * | 12/1980 | Khovaylo .................. 623/22.2 |
| 4,419,026 A | | 12/1983 | Leto |
| 4,435,101 A | * | 3/1984 | Sugiyama et al. .......... 403/122 |
| 4,836,196 A | | 6/1989 | Park et al. |
| 4,854,304 A | | 8/1989 | Zielke |
| 4,887,595 A | | 12/1989 | Heinig et al. |
| 4,887,596 A | | 12/1989 | Sherman |
| 4,946,458 A | | 8/1990 | Harms et al. |
| 5,002,542 A | | 3/1991 | Frigg |
| 5,129,900 A | | 7/1992 | Asher et al. |
| 5,133,717 A | | 7/1992 | Chopin |
| 5,176,680 A | * | 1/1993 | Vignaud et al. ............... 606/61 |
| 5,425,779 A | * | 6/1995 | Schlosser et al. .......... 623/22.2 |
| 5,540,688 A | * | 7/1996 | Navas .......................... 606/61 |
| 5,549,608 A | | 8/1996 | Errico et al. |
| 5,569,247 A | | 10/1996 | Morrison |
| 5,591,166 A | | 1/1997 | Bernhardt et al. |
| 5,628,740 A | | 5/1997 | Mullane |
| 5,716,357 A | | 2/1998 | Rogozinski |
| 5,800,435 A | | 9/1998 | Errico et al. |
| 5,876,459 A | | 3/1999 | Powell |
| 6,022,350 A | * | 2/2000 | Ganem ........................ 606/61 |
| 6,050,997 A | * | 4/2000 | Mullane ....................... 606/61 |
| 6,309,391 B1 | * | 10/2001 | Crandall et al. .............. 606/61 |
| 6,331,179 B1 | * | 12/2001 | Freid et al. ................... 606/61 |
| 6,623,485 B2 | * | 9/2003 | Doubler et al. ............... 606/61 |
| 6,626,906 B1 | * | 9/2003 | Young .......................... 606/61 |

* cited by examiner

*Primary Examiner*—Pedro Philogene
(74) *Attorney, Agent, or Firm*—McHale & Slavin PA

(57) ABSTRACT

An adjustable spinal fixation system is composed of a collection of anchoring assemblies attached, via a variety of connectors, to spine-stabilizing rods. The anchoring assemblies include a linking member attached in a ball-and-socket fashion to a bone-engaging member that is adapted to engage a spinal bone of a patient. The linking member joins one of the included connectors to an associated bone-engaging member. The connectors are selectively attached to one of the stabilizing rods. The anchoring assemblies each include a support collar and a split retention ring that cooperate to allow adjustment of the bone-engaging member and corresponding connector during surgery. When surgery is complete, a securing nut and locking bolt cooperate with the support collar and split retention ring to maintain the relative position of the entire fixation system, preventing unwanted movement between the system components.

3 Claims, 2 Drawing Sheets

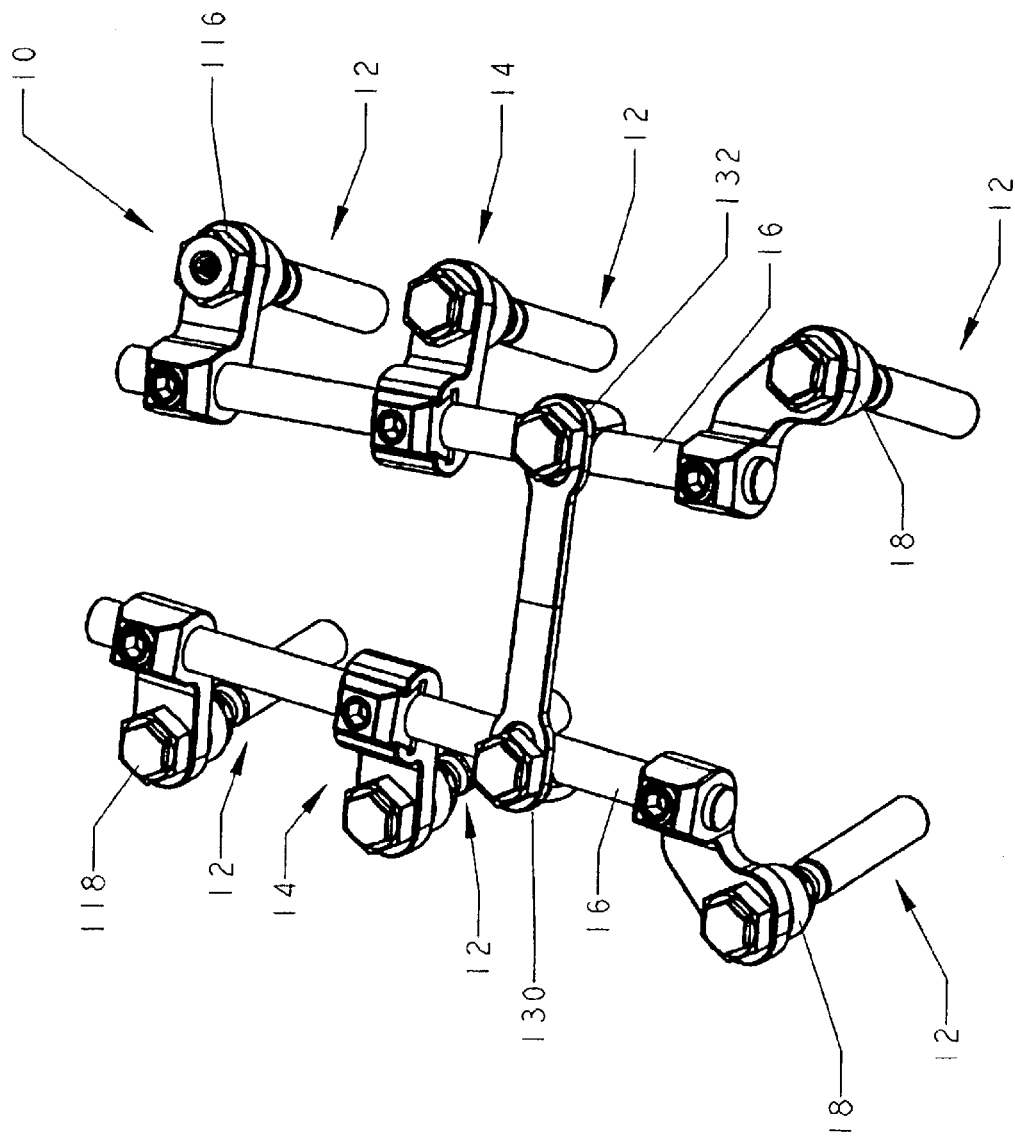

SPLIT RING BONE SCREW FOR A SPINAL FIXATION SYSTEM

This application is a continuation in part of application Ser. No. 09/981,961, filed Oct. 17, 2001 now U.S. Pat. No. 6,623,485.

FIELD OF THE INVENTION

This invention is directed to spinal implant systems and, in particular, to a multi-component adjustable implant system capable of maintaining a desired spacial relationship among the bones of a patient's spine.

BACKGROUND OF THE INVENTION

This application provides improvements to the articulating toggle bolt bone screw disclosed in U.S. Pat. No. 5,628,740, issued to Mullane on May 13, 1997 and U.S. Pat. No. 6,050,997 issued to Mullane on Apr. 18, 2000. The contents of those patents are hereby incorporated by reference.

For individuals with spinal pathologies, the development of spinal fixation devices represents a major medical breakthrough. Surgically implanted fixation systems are commonly used to correct a variety of back structure problems, including those which occur as a result of trauma or improper development during growth. These fixation systems typically include one or more stabilizing rods aligned in a desired orientation with respect to a patient's spine. Additionally, anchoring screws are inserted into the patient's spinal bones, and a series of connectors is used to rigidly link the rods and anchors.

A variety of designs exist, with each design addressing various aspects of the difficulties that arise when one re-shapes an individual's spine to follow a preferred curvature. Unfortunately, known spinal implant systems often correct one set of problems only to create new ones.

Common to spinal implant systems is the necessity for proper anchoring to the bone so as to provide support for the aforementioned components. While bone screws are commonly used for anchoring, they are limited in their positioning due to the design of component pieces. Numerous patents are directed to component design in order to accommodate the bone screw, yet few patents are directed to bone screws that will accommodate existing component design. In many instances the combination of existing component design and bone screw design inhibits application to a particular spinal injury. For example, bone structure of the sacrum is typically soft, and often osteoporotic in the elderly. Perpendicular placement of a bone screw therein may not be possible and placement at an angle thereto may cause undue stress further affecting adjoining bones. Thus, if a common bone screw is employed, the component connector will be of special design.

For this and other reasons, screws located in bone structure typically use a specially designed clamp to attach to a component such as an alignment rod. A problem with specially designed clamps is that bone structure cannot be determined until the patient's bone is exposed causing the necessity of a large inventory of various sized clamps to be on hand during surgery, of which the surgeon must search to find the right combination. Even if a clamp combination is predicted, insertion of the screw may still require angular insertion due to muscle or tender nerve locations. The result is a bone screw which exerts unpredictable forces upon attachment to component connectors. Further, any movement of muscle and other tissue increases the difficulty of the operation and can be a major trauma to a person.

A conventional bone screw consists of a single shaft with a coarse thread at one end for threading into the bone and a machine thread at the other end for coupling to components. Another type of bone screw has a U-shaped top which acts as a saddle for attachment to an alignment rod. If the screw is placed incorrectly for any reason, the rod clamp must be made to accommodate the position.

A number of patents exist which demonstrate the reliance on the saddle type screw support and various designs to accommodate the problem.

U.S. Pat. No. 5,133,717 sets forth a sacral screw with a saddle support. Disclosed is the use of an auxiliary angled screw to provide the necessary support in placing the screw in an angular position for improved anchoring.

U.S. Pat. No. 5,129,900 sets forth an attachment screw and connector member that is adjustably fastened to an alignment rod. An oblong area provided within each connector member allows minute displacement of the alignment rod.

U.S. Pat. No. 4,887,595 discloses a screw that has a first externally threaded portion for engagement with the bone and a second externally threaded portion for engagement with a locking nut. The disclosure illustrates the use of a singular fixed shaft.

U.S. Pat. No. 4,946,458 discloses a screw which employs a spherical portion which is adapted to receive a locking pin so as to allow one portion of the screw to rotate around the spherical portion. A problem with the screw is the need for the locking pin and the inability of the base screw to accommodate a threaded extension bolt.

U.S. Pat. No. 5,002,542 discloses a screw clamp wherein two horizontally disposed sections are adapted to receive the head of a pedicle screw for use in combination with a hook which holds a support rod at an adjustable distance.

U.S. Pat. No. 4,854,304 discloses the use of a screw with a top portion that is adaptable for use with a specially designed alignment rod to permit compression as well as distraction.

U.S. Pat. No. 4,887,596 discloses a pedicle screw for use in coupling an alignment rod to the spine wherein the screw includes a clamp permitting adjustment of the angle between the alignment rod and the screw.

U.S. Pat. No. 4,836,196 discloses a screw with an upper portion design for threadingly engaging a semi-spherical cup for use with a specially designed alignment rod. The alignment rod having spaced apart covertures for receipt of a spherical disc allowing a support rod to be placed at angular positions.

U.S. Pat. No. 5,800,435 sets forth a modular spinal plate assembly for use with polyaxial pedicle screw implant devices. The device includes compressible components that cooperatively lock the device along included rails.

U.S. Pat. No. 5,591,166 discloses an orthopedic bone bolt and bone plate construction including a bone plate member and a collection of fasteners. At least one of the fasteners allows for multi-angle mounting configurations. The fasteners also include threaded portions configured to engage a patient's bone tissue.

U.S. Pat. No. 5,569,247 discloses a multi-angle fastener usable for connecting patient bone to other surgical implant components. The '247 device includes fastening bolts having spherical, multi-piece heads that allow for adjustment during installation of the device.

U.S. Pat. No. 5,716,357 discloses a spinal treatment and long bone fixation apparatus. The apparatus includes link members adapted to engage patient vertebrae. The link members may be attached in a chain-like fashion to connect bones in a non-linear arrangement. The apparatus also includes at least one multi-directional attachment member for joining the link members. This allows the apparatus to be used in forming a spinal implant fixation system.

Another type of spinal fixation system includes rigid screws that engage the posterior region of a patient's spine. The screws are adapted with rod-engaging free ends to engage a support rod that has been formed into a desired spine-curvature-correcting orientation. Clamping members are often used to lock the rod in place with respect to the screws. Instead of clamping members, other fixation systems, such as that disclosed in U.S. Pat. No. 5,129,900, employ connectors that join the support rods and anchoring screws. The connectors eliminate unwanted relative motion between the rod and the screws, thereby maintaining the patient's spine in a corrected orientation.

Unfortunately, although these so-called "rigid screw" fixation systems can alter the curvature of a patient's spine, they can also be difficult to install. In this type of system, the anchoring screws must be secured in a region that is strong/rigid enough to support the characteristically-large loads typically transferred from the support rods. As a result, the number of suitable anchoring locations is limited. Typically, these screws are anchored into the posterior region of a patient's spinal column or into pedicle bone. With rigid screw systems, installation requires bending a support rod into a path that will not only correct the shape a patient's spine but that will also engage each of the installed anchoring screws. Achieving a proper fit between all of the components while contending with the constraints encountered during surgery is often difficult. In severe cases, a suitable fit may not be achieved and the surgery will be unsuccessful.

Additionally, the nature of the installation process required for rigid screw fixation systems often subjects the system components to pre-loading that unduly stresses the interface between the patient's bone and the employed anchoring screws. With these designs, as a patient moves about during daily life, the system components may become separated from the supporting bone. Corrective surgery to reattach anchoring screws exposes an already-weakened region to additional trauma and presents the risk of additional damage.

Other spinal fixation systems employ adjustable components. For example, U.S. Pat. No. 5,549,608 includes anchoring screws that have pivoting free ends which attach to discrete rod-engaging couplers. As a result, the relative position of the anchoring screws and rods may be adjusted to achieve a proper fit, even after the screw has been anchored into a patient's spinal bone. This type of fixation system succeeds in easing the rod-and-screw-linking process. This adjustment capability allows the screws to accommodate several rod paths. Unfortunately, some adjustable fixation systems tolerate only limited amounts of relative adjustment between components, operating best when loaded in one of several preferred arrangements. As a result, many prior art adjustable fixation systems are suitable for only a few situations.

Additionally, many adjustable fixation systems are prone to post-surgery component loosening. As a patient moves about during day-to-day living, his spine is subjected to a seemingly-endless amount of dynamic loading. Almost all activity requires some form of back motion; over time, this cyclic movement tends to work the components of many adjustable fixation systems loose.

Some adjustable spinal fixation systems include locking mechanisms designed for long-term, post-surgery securement of the system components. Although capable of being locked in place, these systems are often difficult to secure, requiring an excess of tools during the installation process. The need for extra tools, such as those required to shave or crimp key portions of a fixation system, increasing surgical risk by adding complexity and increasing the number of required steps. Although locking-component fixation systems exist, many of them unduly increase the dangers of back implant surgery to an unacceptable level.

Hardware-intensive fasteners are disclosed in U.S. Pat. No. 5,549,608, in which anchoring screws are fitted with wrenching flats that allow an anchoring screw to be attached to a patient's spinal bone with the flats being trimmed away once the screw is in place. Clamping nuts are then used to secure the anchoring screws to included stabilizing rods.

Additionally, many spinal fixation systems do not permit component repairs. If, for example, a threaded portion of a connecting member becomes stripped or cross-threaded, the entire connector must be slid off of the associated stabilizing rod. Often, such removal produces an undesirable "domino-effect," requiring that several connectors be slid off to allow removal of the damaged connector. Such requirements add unnecessary difficulty to an already-complex procedure.

The bone screws shown and described in U.S. Pat. No. 5,628,740 and U.S. Pat. No. 6,050,997 have a bone screw with a spherical cavity in the proximal end. A toggle bolt with a spherical distal end is inserted into the cavity in the bone screw. A collet is forced into the spherical cavity superior to the spherical end of the toggle bolt. A support collar or attachment cap is placed over the toggle bolt and tightened down. This forces the retention collet to engage the spherical portion of the toggle bolt and the inside of the spherical cavity locking the toggle bolt in a selected angular disposition. This system requires extremely accurate machining of the threaded components to result in an optimum frictional fit. Further, because the collet is a ring, with a fixed inner diameter, there is only one correct size for the spherical components. Finally, any deformation of the ring will lessen the over-all frictional contact by creating wrinkles or ridges on the collet.

U.S. Pat. No. 5,876,459 to Powell teaches the use of a deformable collet to form a friction lock between components of an artificial hip. The collet is expanded outwardly to frictionally fix an artificial trochanter onto the neck of a ball joint.

U.S. Pat. No. 4,419,026 to Leto discloses a split ring camming internal locking device used with telescoping tubular members for transporting liquids. The ring is split for flexing to fit around the internal tube and for resiliently sealing against the external tube.

Thus, what is needed is a spinal fixation system that includes the advantages of known devices, while addressing the shortcomings they exhibit. The system should allow component adjustment during installation, thereby enabling satisfactory correction of a wide variety of spinal deformities. The system should also include a component locking mechanism that is simple and reliable. The system should include two-piece connectors that may be mounted along a support rod, in-between previously-secured connectors. The system should also include mounting hardware that secures with a minimum of tools and that allows modular replacement of components damaged during installation.

SUMMARY OF THE INVENTION

The present invention is a bone screw for use in a spinal fixation system for reshaping the spine of a patient. The bone screw has threads on one end for anchoring in the spine. The other end has a spherical connector with a rounded exterior and a ball-shaped cavity therein. The cavity has a larger diameter equator and a narrower mouth. The mouth of the ball-shaped cavity accepts the tapered end of a toggle bolt such that the toggle bolt and the bone screw are connected by a ball joint. The tapered end of the toggle bolt tapers from a larger end toward a narrower threaded shank. To prevent disassembly of the bone screw and toggle bolt, an associated split retention ring locking mechanism is inserted in the ball-shaped cavity between the tapered end of the toggle bolt and the mouth of the cavity. The resilient split retention ring has a spherical outer surface and a tapered aperture therethrough. The taper of the aperture is complimentary to the taper of the toggle bolt. The tapered end of the toggle bolt is inserted through the split retention ring. The ring can be compressed to reduce it's diameter for insertion through the narrower mouth of the cavity and then expands to fill the ball-shaped cavity about the tapered end of the toggle bolt.

Because of the flexibility and resilience of the split retention ring, the mating parts do not require fine tolerances and are less expensive to make. Further, the split retention ring provides infinite adjustment of the locking pressure as the toggle bolt is tightened into the assembly. The system is modular, employing a collection of anchoring assemblies that are linked, via various connectors, to strategically-arranged stabilizing rods. The stabilizing rods are shaped and aligned to impart a preferred curvature to a patient's spine.

The anchoring assemblies are multi-piece units characterized by linking members that are joined in a ball-and-socket-type arrangement with a corresponding bone-engaging member. During use, the bone-engaging member is secured to a spinal bone and the linking member is secured to one of the stabilizing rods via a corresponding connector. The bone-engaging member may include coarse, external threads or have a hook-shaped end. Each anchoring assembly also includes a support collar that provides a secure interface between the bone-engaging member and associated connector. Each anchoring assembly also includes a securing nut and a locking bolt that cooperate to prevent unwanted, post-installation motion within the anchoring assembly. The securing nut and locking bolt also prevent unwanted relative motion between the anchoring assembly and associated connector.

The connectors are rigid structures adapted to link an associated anchoring assembly with one of the stabilizing rods. In one embodiment, the connectors are two-piece constructions that allow the connector to engage a stabilizing rod in a sandwich-type arrangement, permitting connector installation and removal that does not disturb adjacent connectors.

The stabilizing rods are rigid members shaped to form a spine-curvature-correcting path. Attaching each anchoring assembly, via connectors, to a stabilizing rod forces a patient's back into a surgeon-chosen shape. Stabilizing rods may be used singly, or in pairs, depending upon the type of correction required. The rods vary in size, but typically extend between at least two vertebrae.

Thus, it is an objective of the present invention to provide a bone screw assembly for a spinal fixation system that permits component adjustment during installation, thereby enabling satisfactory correction of a wide variety of spinal deformities.

It is an additional objective of the present invention to provide a bone screw assembly that includes a split ring locking mechanism that is simple and reliable. The split ring has a tapered aperture and a spherical outer surface to mate with the tapered end of a toggle bolt.

It is a further objective of the present invention to provide a spinal fixation system that includes two-piece connectors that may be mounted along, and removed from, a support rod without requiring movement of adjacent connectors.

It is yet another objective of the present invention to provide a spinal fixation system that includes mounting hardware which requires a minimum number of tools.

It is also an objective of the present invention to provide a spinal fixation system that allows modular replacement of damaged components.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

BRIEF DESCRIPTION OF THE DRAWINGS

FIG. 1 is a pictorial view of the spinal fixation system of the present invention;

DETAILED DESCRIPTION OF THE PREFERRED EMBODIMENT

Figure 3:
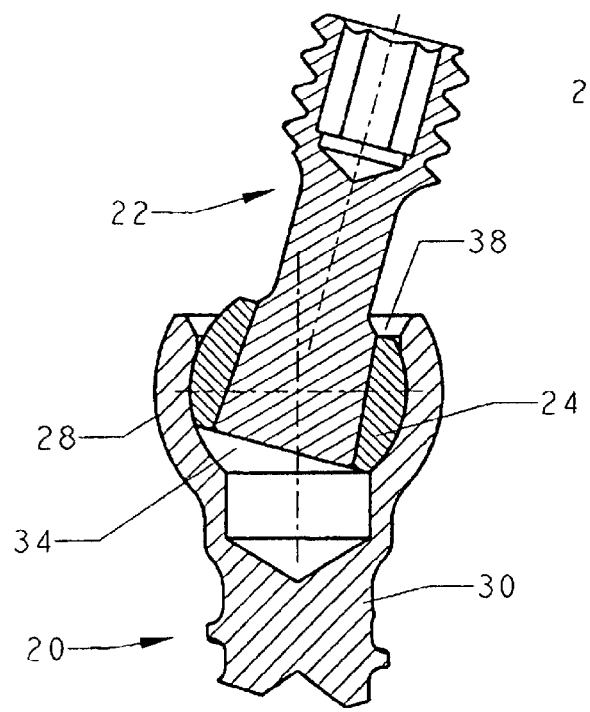
FIG. 3 is a cross section of the connector of this invention.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown in the drawings and described in the specification.

Now with reference to FIG. 1, the spinal fixation system 10 of the present invention is shown. By way of overview, the Fixation System 10 includes a collection of bone-engaging anchoring assemblies 12 that are joined via connectors 14,14' to stabilizing rods 16, 16'. The specifics of the spinal fixation system 10 will now be discussed in more detail.

Figure 2:
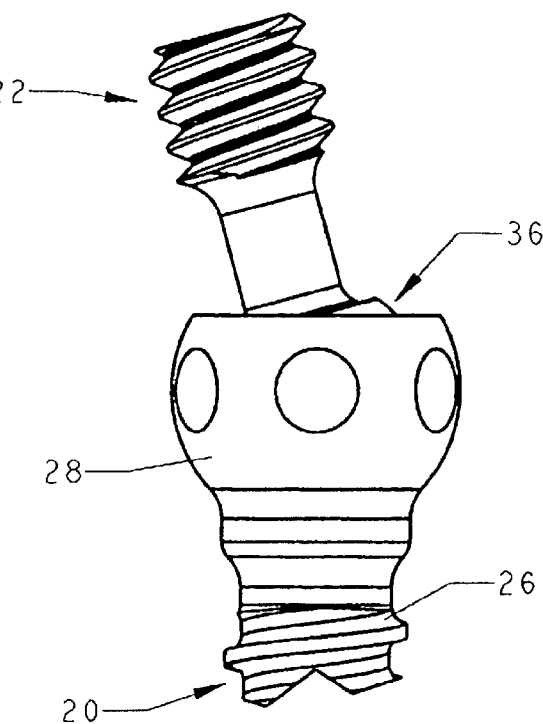
FIG. 2 is a perspective view of an anchoring assembly used in the present spinal fixation system.

With additional reference to FIG. 2, one of the included anchoring assemblies 12 is shown in an assembled state. Each anchoring assembly 12 also includes a pedicle screw 20, a toggle bolt 22, and a split retention ring 24. Each pedicle screw 20 also includes a ball end 28 spaced apart from the threaded end 26 by a neck portion 30. The exterior 32 of the pedicle screw ball end 28 is preferably contoured for easy grasping. The interior of the pedicle screw ball end 28 forms a retention cavity 34, discussed below. The entrance 36 to the retention cavity 34 is characterized by a securing lip 38 that extends radially into the retention cavity 34.

Figure 5:
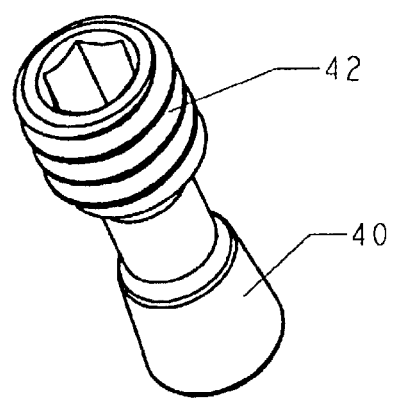
FIG. 5 is a perspective view of an the toggle bolt of the present invention.

Each toggle bolt 22, as shown in FIG. 5, includes a tapered end 40 and an opposite threaded end 42. As seen in FIG. 3, the tapered end 40 of the toggle bolt 22 is shaped and sized to fit inside the pedicle screw retention cavity 34. Preferably, the interior of the retention cavity is substantially spherical but of larger dimensions than the tapered contour of the toggle bolt end 40.

Figure 4:
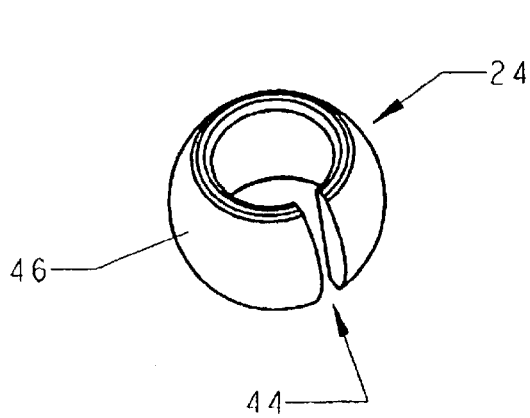
FIG. 4 is a perspective of the split ring connector.

With reference to FIG. 4, the split retention ring 24 has a substantially spherical outer surface and a tapered inner wall. The ring includes a gap 44 separating the opposite ends of the split retention ring main body 46. As seen in FIG. 3, the split retention ring 24 is used as a bracing means to secure the tapered end 40 of the toggle bolt 22 within the pedicle screw retention cavity 34. More specifically, after the toggle bolt tapered end 40 is placed within the pedicle screw retention cavity 34, the split retention ring 24 is placed about the shank of the toggle bolt and pushed through the entrance 36 of the retention cavity 34 by reducing the gap 44 facilitating travel past the engagement lip 38, thereby bringing the split retention ring main body 46 to rest against the engagement lip by spring action resilience of the split retention ring 24.

With this arrangement, the split retention ring 24 allows universal movement of the toggle bolt 22 within the retention cavity 34, while preventing removal of the toggle bolt therefrom. Once the split retention ring 24 and toggle bolt 22 are in place, the threaded end 42 of the toggle bolt is inserted through a passthrough aperture of the support collar 18 (not shown).

Once the toggle bolt 22 has been passed through the support collar, the support collar comes to rest against the pedicle screw ball end 28. Although several shapes are possible, the interior of the support collar preferably has a spherical contour that matches the exterior 32 of the pedicle screw ball end 28. This arrangement limits the relative motion possible between the support collar and the toggle bolt 22, while allowing the split ring 24 to rotate freely within the pedicle screw retention cavity 34. Although an assembly process has been described above, the anchoring assemblies 12 are typically delivered to the end-user surgeon as a finished unit.

With additional reference to FIG. 3, the interior bore 122 of the toggle bolt threaded end 42 has a hexagonal cross section. This allows the insertion of an allen wrench, not shown, into the interior bore 122 to hold the connection and prevent relative motion between the tapered end 40 of the toggle bolts 22 and the spherical retention cavity 34 of the pedicle screw 20. The inserted allen wrench thereby prevents unwanted spinning of the toggle bolt 22 within the retention cavity 34 while the securing nut 116 is tightened onto the exterior threads 120.

Tightening the securing nut 116 forces the toggle bolt threaded end 42 to travel longitudinally through the passthrough aperture (not shown) and also causes the toggle bolt tapered end 40 to be forced against the split retention ring 24 with the longitudinal movement reducing the gap 44. Further tightening of the securing nut 116 forms a substantially rigid fit between the toggle bolt 22 and the pedicle screw 20. With the securing nut 116 tightened appropriately, the toggle bolt threaded end 42 is locked in place with regard to the right-facing straight connector attachment flange, and the toggle bolt tapered end 40 is locked in place within the pedicle screw retention cavity 34. In this state, the split retention ring is sandwiched between the exterior of the toggle bolt ball end 40 and the ball-shaped interior of the retention cavity 34. Since the split retention ring 24 is locked within the retention cavity 34 by the retention cavity engagement lip 38, relative motion between the toggle bolt tapered end and the pedicle screw 20 is prevented once the toggle bolt threaded end 42 is locked in place by the tightened securing nut 116. This results in a rigid link between the right-facing straight connector and the anchoring assembly 12.

Although the above description refers to joining an anchoring assembly 12 specifically to a right-facing straight connector 52, each of the one-piece connectors 14 and two-piece connectors 141 may be attached to an anchoring assembly in a similar manner. That is, right-facing offset connectors are attached by inserting a toggle bolt threaded end through the associated passthrough aperture ; left-facing offset connectors are joined with an anchoring assembly by inserting a toggle bolt threaded end through an associated passthrough aperture; and left-facing straight connectors are attached to anchoring assemblies by inserting a toggle bolt threaded end through an associated passthrough aperture. In each case, the exterior threads 120 of the inserted toggle bolt threaded end 42 are held in place by a tightened securing nut 116, as described previously.

To prevent unwanted loosening of a connector 14, 14' and anchoring assembly 12 union, a locking bolt 118 is inserted into the threaded interior bore 122 of the toggle bolt corresponding to each anchoring assembly that has been secured in place. As mentioned above, each locking bolt 118 has a left-handed thread pattern, thereby matching the left-handed thread pattern of each toggle bolt threaded interior bore 122. The locking bolt 118 is screwed into an associated toggle bolt threaded interior bore 122 until the locking bolt head plate comes to rest against the securing nut 116 that holds the corresponding anchoring assembly 12 in place with respect to the associated connector 14, 14'. Incorporating this locking bolt 118 ensures that anchoring assemblies 12 and connectors 14, 14' stay locked in place, thereby preventing unwanted relative motion within the spinal fixation system 10.

In all other respects, the split ring bone screw of this invention may be deployed with other fixation apparatus as shown and described in the parent application, Ser. No. 09/981,961, incorporated herein by reference.

Although the invention has been described in terms of a specific embodiment, it will be readily apparent to those skilled in this art that various modifications, rearrangements and substitutions can be made without departing from the spirit of the invention. The scope of the invention is defined by the claims appended hereto.

What is claimed is:

1. In an anchoring assembly for insertion in skeletal bone, said anchoring assembly having a linking member having a threaded first end for engaging a securing nut and a tapered second end;

a bone-engaging member having a first end adapted to engage said bone and a second end comprising a retention cavity constructed and arranged to engage said linking member second end, said retention cavity having a substantially-spherical exterior surface and a circular open mouth, the improvement comprising said retention cavity has a spherical inside wall, said wall narrowing toward said circular mouth;

a bracing device in said retention cavity for universal movement within said retention cavity, said bracing device in the form of a split retention ring having a diameter greater than the diameter of said circular open mouth, said split retention ring mounted within said circular mouth of said retention cavity, said split retention ring comprising a main body having a tapered aperture therethrough and a gap, the tapered aperture being complementary to said taper of said linking member second end, thereby preventing removal of said linking member second end from within said retention cavity, and adapted to frictionally engage said linking member second end;

whereby tightening of said securing nut draws said linking member second end against said split retention ring forcing said split retention ring along said narrowing spherical inside wall reducing said gap and applying progressive pressure on said linking member and selectively prevents relative motion between said linking member and said bone-engaging member.

2. In an anchoring assembly of claim 1, wherein said first end of said bone-engaging member has screw threads to engage said bone.

3. In an anchoring assembly for use with a spinal fixation system, said spinal fixation system including at least one spine stabilizing rod and at least one connector adapted to selectively engage said at least one stabilizing rod;

a linking member having a threaded first end and a tapered second end, said threaded first end being sized to engage said connector;

a bone-engaging member having a first end adapted to engage said bone and a second end comprising a retention cavity constructed and arranged to engage said linking member second end, said retention cavity having a substantially-spherical interior surface and exterior surface;

a locking means for attaching said linking member second end to said connector;

the improvement comprising a bracing device resiliently disposed in said retention cavity for universal movement of said linking member second end in a chosen orientation within said retention cavity, said bracing device in the form of a split retention ring, said retention ring having a substantially spherical exterior surface, said interior surface of said retention ring forming a tapered aperture, exterior surface, said interior surface of said retention ring forming a tapered aperture, said exterior surface of said retention ring complementary to said interior surface of said retention cavity, said tapered aperture complementary to said tapered second end of said linking member, said bracing member positioned between said tapered second end and said interior surface of said retention cavity;

whereby said bracing device prevents relative motion between said anchoring assembly and said connector once said anchoring assembly and said connector have been arranged in a spinal-curve-correcting orientation.

* * * * *